(12) United States Patent
Nussbaum

(10) Patent No.: US 10,391,273 B2
(45) Date of Patent: Aug. 27, 2019

(54) SLEEP APNEA DEVICE TO POSITIVELY BLOCK EXHALING AND METHOD OF USE

(71) Applicant: Eliezer Nussbaum, Huntington Beach, CA (US)

(72) Inventor: Eliezer Nussbaum, Huntington Beach, CA (US)

(73) Assignee: The Regents of the University of California, Oakland, CA (US)

( * ) Notice: Subject to any disclaimer, the term of this patent is extended or adjusted under 35 U.S.C. 154(b) by 343 days.

(21) Appl. No.: 14/746,357

(22) Filed: Jun. 22, 2015

(65) Prior Publication Data

US 2016/0051397 A1    Feb. 25, 2016

Related U.S. Application Data

(63) Continuation-in-part of application No. 14/610,835, filed on Jan. 30, 2015, now abandoned.

(51) Int. Cl.
*A61F 5/56* (2006.01)
*A61M 16/20* (2006.01)
*A61M 16/06* (2006.01)

(52) U.S. Cl.
CPC ............ *A61M 16/208* (2013.01); *A61F 5/56* (2013.01); *A61M 16/0605* (2014.02); *A61M 16/0666* (2013.01)

(58) Field of Classification Search
CPC ...... A61M 15/00; A61M 16/00; A61M 16/06; A61M 16/0616; A61M 16/0622;
(Continued)

(56) References Cited

U.S. PATENT DOCUMENTS

| 238,793 A | 3/1881 | Leslie |
| 4,782,832 A | 11/1988 | Trimble |

(Continued)

FOREIGN PATENT DOCUMENTS

| CN | 203989337 U | 12/2014 |
| JP | 2008055232 | 3/2008 |

(Continued)

OTHER PUBLICATIONS

ISA/U.S.; Written Opinion and ISR in PCT International Application PCT/US15/46608 dated Nov. 30, 2015.
(Continued)

*Primary Examiner* — Victoria J Hicks
(74) *Attorney, Agent, or Firm* — Fulwider Patton LLP

(57) ABSTRACT

Nasal cannula devices formed with through air-flow passages and circular membranes anchored centrally to retainers and operative upon inhaling by the patient to raise off the peripheral edges of respective seats for free flow of air into the nasal passages and, further, operative upon exhalation by the patient to seat on the seats.
The invention further includes a method introducing the cannula devices with cushioning rings to cushion against the walls of the walls of the nasal passages.
In another method the invention includes manufacturing a barrel with proximal and distal glands to friction fit on a shell formed in the body of the cannula and receiving an annular retainer friction fit in the distal cannula to mount a sealing membrane.

18 Claims, 10 Drawing Sheets

(58) Field of Classification Search
CPC .......... A61M 16/0666; A61M 16/0672; A61M 16/0683; A61M 16/20; A61M 16/201; A61M 16/207; A61M 16/208
USPC ..... 128/846, 857, 858, 863, 200.24, 201.18, 128/203.12, 203.11, 203.18, 203.22, 128/206.11, 207.18; 623/1.24, 1.26, 2.12, 623/2.17, 2.2, 2.21, 2.22, 2.24, 2.27, 2.28; 137/15.06, 15.17, 15.18, 216, 217, 234.5, 137/248, 454.5, 508, 510, 515.3, 516.15, 137/516.17
See application file for complete search history.

(56) References Cited

U.S. PATENT DOCUMENTS

| | | | |
|---|---|---|---|
| 5,269,296 A | 12/1993 | Landis | |
| 5,335,654 A | 8/1994 | Rapaport | |
| 5,477,852 A | 12/1995 | Landis | |
| 5,501,214 A | 3/1996 | Sabo | |
| 5,535,739 A | 7/1996 | Rapoport | |
| 5,687,715 A | 11/1997 | Landis | |
| 5,740,799 A | 4/1998 | Nielsen | |
| 5,806,515 A | 9/1998 | Bare | |
| 6,478,026 B1 | 11/2002 | Wood | |
| 6,527,011 B1 | 3/2003 | Mantz | |
| 7,059,327 B2 | 6/2006 | Worthington | |
| 7,188,624 B2 | 3/2007 | Wood | |
| 7,559,326 B2 | 7/2009 | Smith | |
| 7,798,148 B2 | 9/2010 | Doshi | |
| 7,856,979 B2 | 12/2010 | Doshi | |
| 7,992,564 B2 * | 8/2011 | Doshi | A61M 15/08 128/200.24 |
| 8,051,856 B2 | 11/2011 | Bare | |
| 8,136,527 B2 | 3/2012 | Wondka | |
| 8,181,651 B2 | 5/2012 | Pinel | |
| 8,365,736 B2 | 2/2013 | Doshi | |
| D678,510 S | 3/2013 | Koschany | |
| 9,072,855 B2 | 7/2015 | McAuley et al. | |
| 9,095,735 B2 * | 8/2015 | Kashmakov | A62B 23/06 |
| 9,220,628 B2 | 12/2015 | Bergstrand Borjegren et al. | |
| 9,408,630 B2 | 8/2016 | Alexander et al. | |
| 9,631,799 B2 | 4/2017 | Chien et al. | |
| 2006/0144398 A1 | 7/2006 | Doshi et al. | |
| 2007/0227542 A1 | 10/2007 | Kashmakov | |
| 2009/0032028 A1 * | 2/2009 | Bare | A61M 16/0468 128/207.16 |
| 2009/0095303 A1 | 4/2009 | Sher et al. | |
| 2009/0126738 A1 | 5/2009 | Hoogenakker et al. | |
| 2009/0194100 A1 * | 8/2009 | Minagi | A61F 5/08 128/200.24 |
| 2009/0308402 A1 | 12/2009 | Robitaille | |
| 2011/0067709 A1 | 3/2011 | Doshi | |
| 2011/0100369 A1 | 5/2011 | Zhang | |
| 2011/0218451 A1 | 9/2011 | Lai et al. | |
| 2012/0055488 A1 | 3/2012 | Pierce et al. | |
| 2012/0073576 A1 | 3/2012 | Wondka | |
| 2012/0125332 A1 | 5/2012 | Niland | |
| 2013/0019870 A1 * | 1/2013 | Collazo | A61M 16/0666 128/205.24 |
| 2013/0079870 A1 * | 3/2013 | Roeder | A61F 2/07 623/1.35 |
| 2013/0081637 A1 * | 4/2013 | Foley | A61F 5/08 128/848 |

FOREIGN PATENT DOCUMENTS

| | | |
|---|---|---|
| JP | 2013128851 | 7/2013 |
| KR | 2002064400 | 8/2008 |

OTHER PUBLICATIONS

Kearns, Michael D., Prior Art Search—"Improved Sleep Apnea Device", Aug. 15, 2016.

* cited by examiner

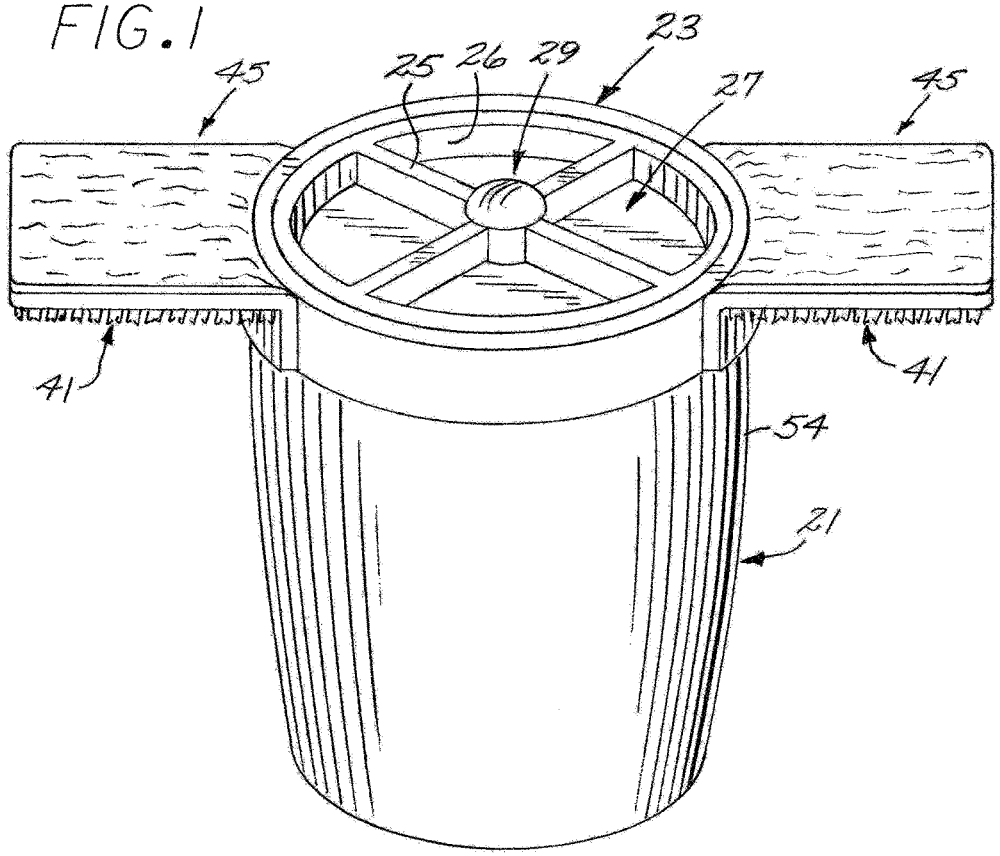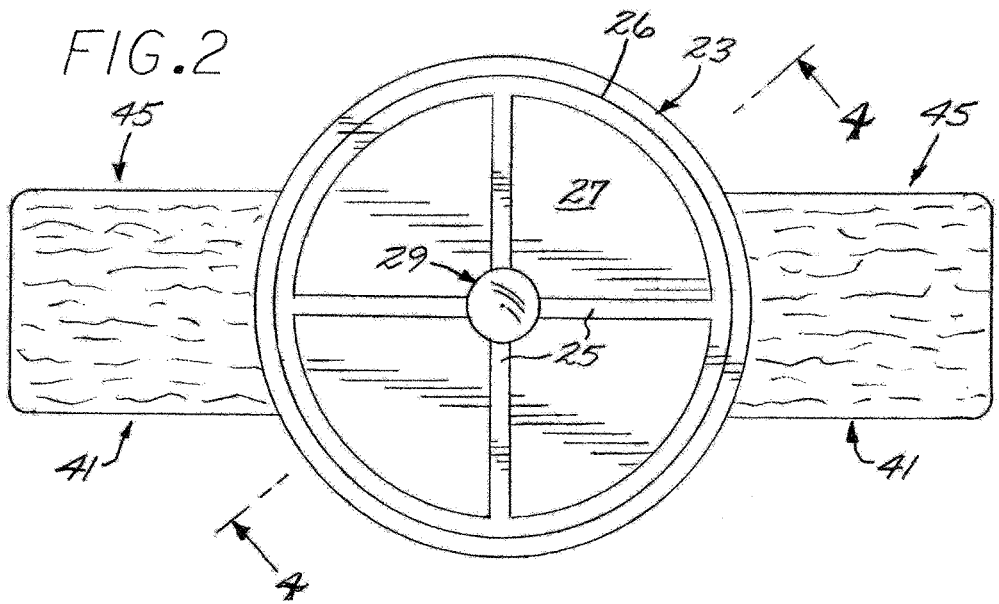

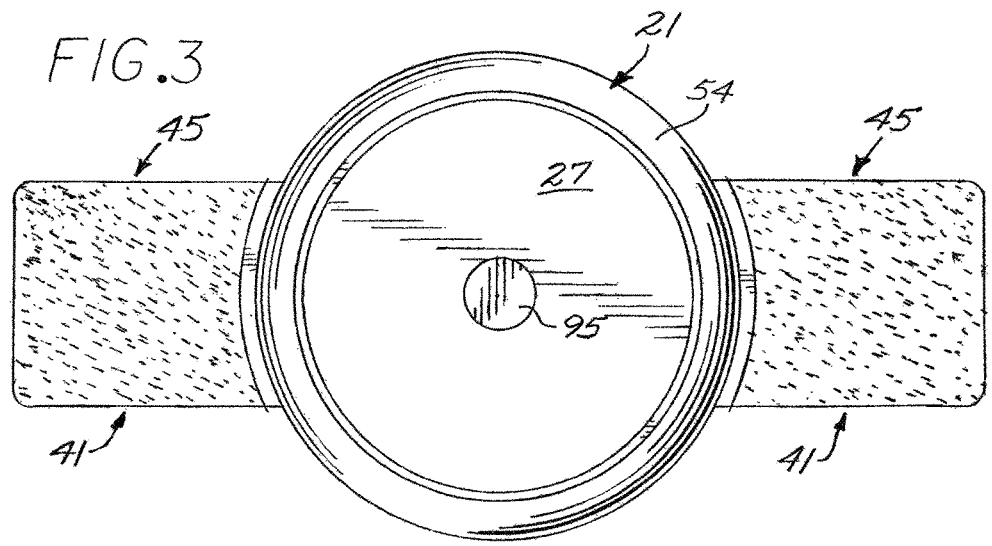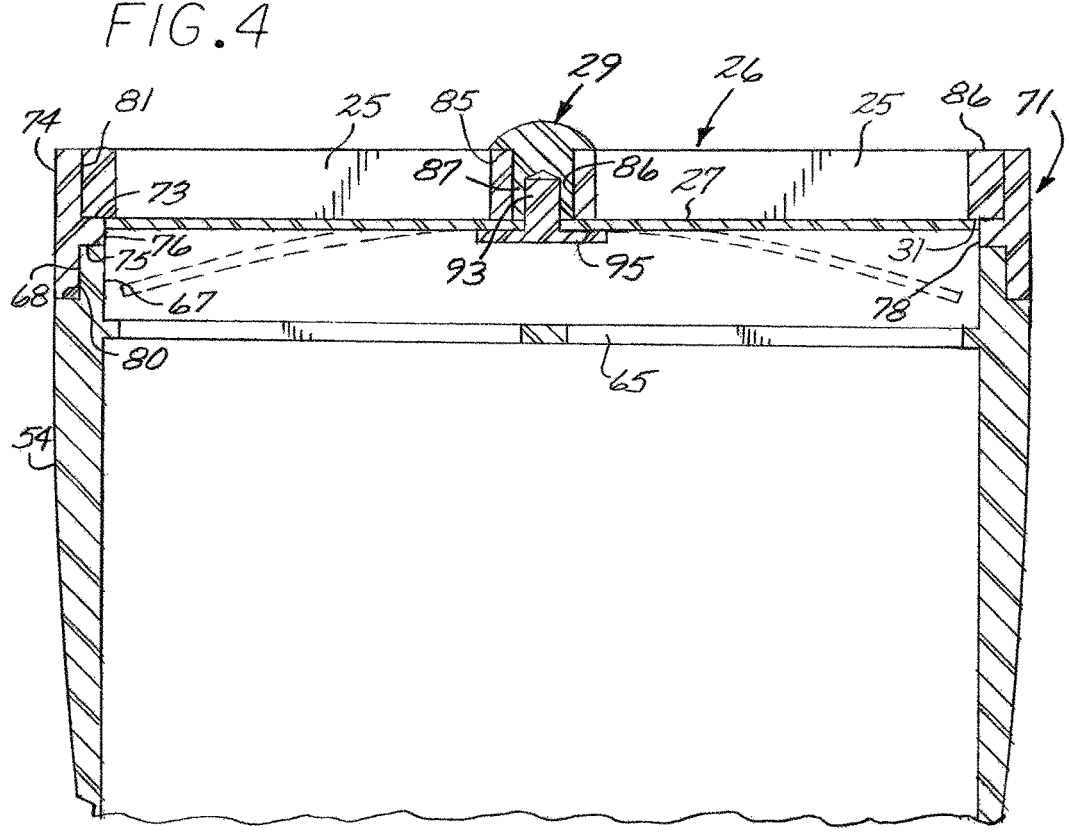

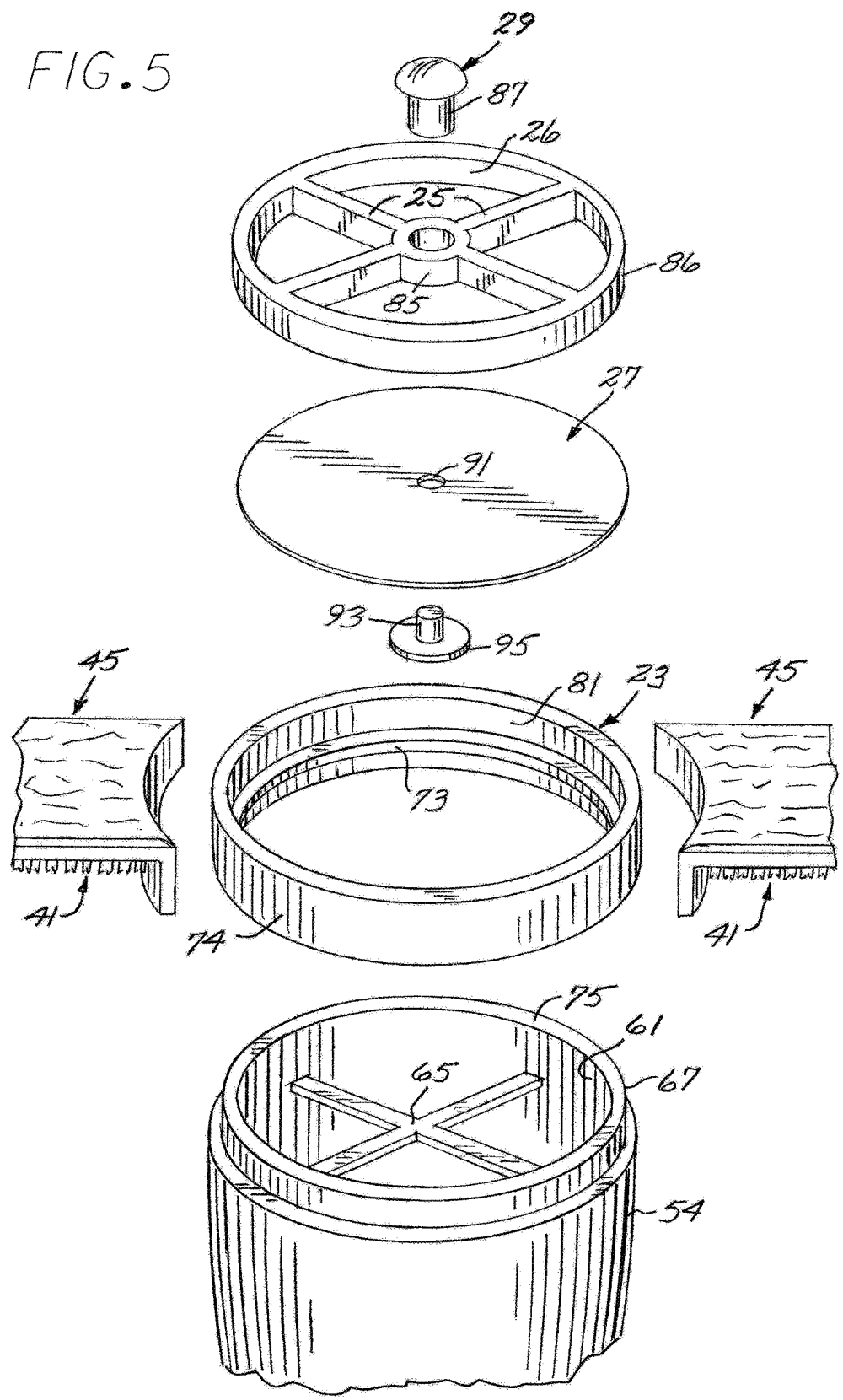

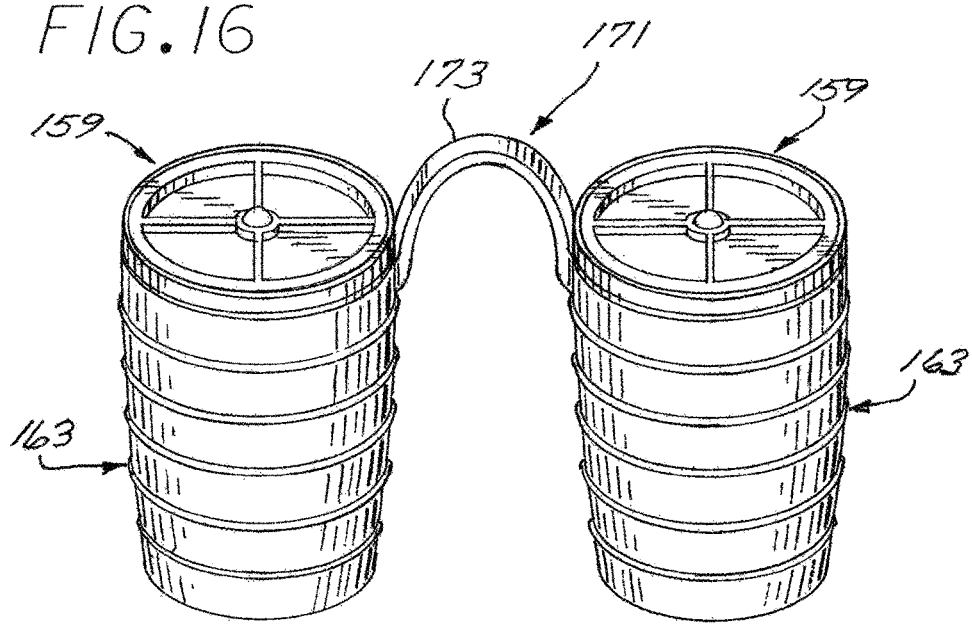
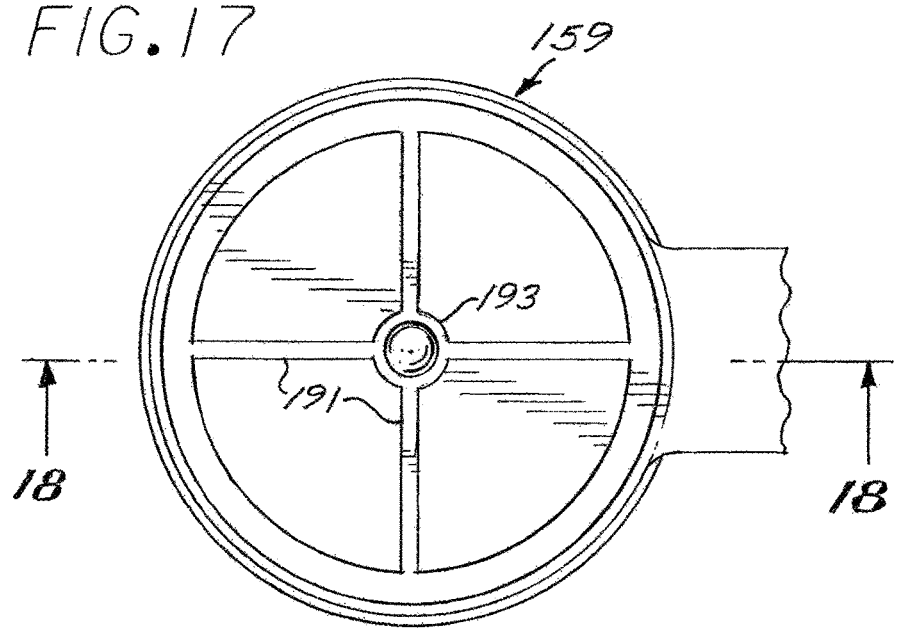

SLEEP APNEA DEVICE TO POSITIVELY BLOCK EXHALING AND METHOD OF USE

CROSS-REFERENCE TO RELATED APPLICATIONS

This application is a continuation-in-part of co-pending U.S. application Ser. No. 14/610,835 filed Jan. 30, 2015, the entire contents of which are incorporated by reference herein and priority is claimed thereto.

BACKGROUND OF THE INVENTION

Field of the Invention

The present invention relates to sleep apnea devices and particularly to the type inserted in the nasal passages to control exhaling by the patient.

Description of the Related Art

Apnea is a Greek term meaning "without breath". Simply stated apnea means cessation to breathing, something that may lead to decreased oxygen saturation (hypoxia) and an accumulation of carbon dioxide in the bloodstream. Hundreds of millions of patients are afflicted with sleep apnea, a dangerous condition which can lead to sleep deprivation and the consequent unhealthy existence and even death.

There are three types of sleep apnea: Obstructive, Central and mixed. Obstructive sleep apnea is the more common of the two. Obstructive Sleep Apnea can occur as repetitive episodes of complete or partial upper airway blockage during sleep. During an apnea episode, the diaphragm and chest muscles work harder as the pressure increases to open the airway. Breathing frequently resumes with a loud gasp or body jerk. These episodes can interfere with sound sleep, reduce the flow of oxygen to vital organs, and cause heart rhythm irregularities.

In Central Sleep Apnea, the airway is not blocked but the brain fails to signal the muscles to read due to instability in the respiratory center. This affliction is not addressed by the present invention.

Mixed sleep apnea is combination of both obstructive and central.

While Obstructive Sleep Apnea (OSA) is commonly associated with obesity and the male gender, it affects a broad cross-section of the population. Other risk factors include habitual snoring, which is often a precursor of more serious upper respiratory disorders such as Obstructive Sleep Apnea. In fact, results from a recent study indicate that 1 in 3 men and 1 in 5 women who snore habitually suffer from some degree of Obstructive Sleep Apnea.

Symptoms of OSA may be recognized by the bed partner or the patient him or herself. The most common symptoms include snoring, daytime sleepiness or fatigue, restlessness during sleep, sudden awakening with a sensation of gasping or choking, dry mouth or sore throat upon awakening, intellectual impairment, such as trouble concentrating, forgetfulness or irritability, night sweats, sexual dysfunction and headaches.

Left untreated sleep apnea can result in a number of health problems including hypertension, stroke, arrhythmias, cardiomyopathy (enlargement of the muscle tissue of the heart), congenital heart failure, diabetes, and heart attacks. In addition, the untreated sleep apnea may be responsible for job impairment, work related accidents, and motor vehicle crashes as well as academic underachievement in children and adolescents. The risks are significantly increased for those suffering from obesity, chronic lung disease, cardiac disease or COPD.

Obstructive Sleep Apnea Syndrome (OSAS) is a debilitating sleep and breathing disorder which can lead to numerous different afflictions sometimes resulting in stroke, heart attack or other ailments. Debilitating sleep and breathing disorder has been defined as the cessation of breathing for 10 seconds or more (an apnea) at least five times per hour of sleep. Apnea Hypopnea Index (AHI) is the average number of apnea intervals per hour. An AHI of 5 is considered very minimal, less than 15, mild, 30, moderate and over 30, severe.

It is known that the body and muscles relax which can cause excess tissue to collapse into the upper airway (back of the mouth, nose and throat) and block breathing. When breathing is interrupted by an obstruction in the airway, the body reacts by waking enough to start breathing again. These arousals may occur hundreds of times each night but do not fully awaken the patient, who remains unaware of the loud snoring, choking and gasping for air that are typically associated with Obstructive Sleep Apnea Syndrome. Obstructive Sleep Apnea sufferers never get "a good night of sleep" because repeated apneas and arousals deprive patients of REM and deep-stage sleep leading to chronic daytime exhaustion and long-term cardiovascular stress.

Obstructive Sleep Apnea has a profound impact on an individual's health. Excessive daytime sleepiness caused by disruption of normal sleep patterns leads to a significant increase in the rate of accidents for afflicted patients, including a seven fold increase in automobile accidents. Over the long term, Obstructive Sleep Apnea is associated with greater risk of hypertension and cardiovascular disease. The National Commission on Sleep Disorders Research estimates that 3800 cardiovascular deaths due to sleep apnea occur each year. In addition, loud snoring and intermittent breathing interruptions can affect the quality of sleep of the Obstructive Sleep Apnea patient's bed partner. Witnessing an apnea can be a frightening experience because the Obstructive Sleep Apnea patient appears to be suffocating.

24% of adult men and 9% of adult women, or more than 20 million Americans, are estimated to have some degree of Obstructive Sleep Apnea. Of these, six million are estimated to have cases severe enough to warrant immediate therapeutic intervention. However, Obstructive Sleep Apnea was not well understood or recognized by physicians until recently and only a fraction of these 20 million Obstructive Sleep Apnea patients have been diagnosed and treated by a physician. The number of patients currently undergoing treatment is probably on the order of one million.

Hypertension refers to elevated blood pressure and is a common disease, characterized by elevated systolic and/or diastolic blood pressure. Despite the prevalence of hypertension and its associated complications, control of the disease is somewhat inadequate. Only a third of the population suffering with hypertension control their blood pressure adequately. OSA, left untreated can lead to hypertension.

It is known that various forms of positive airway pressure during sleep can provide an effective form of therapy for apnea sufferers. Approaches taken have been to apply Continuous Positive Airway Pressure (CPAP) in which a positive pressure is maintained in the airway throughout the respiratory cycle or Bi Level Positive Airway Pressure (BiPAP) in which positive pressure is maintained during inspiration but reduced during expiration. Intermittent mechanical positive pressure ventilation can be provided where pressure is applied when an episode of apnea is sensed. Positive airway pressure devices have traditionally employed either a face mask to cover the patient's nose or nasal pillows as the interface between a ventilation device and the patient's airways. These interfaces suffer the shortcoming that they are sometimes cumbersome and uncomfortable to wear, often leading to rejection by the patient.

The face mask typically requires a harness, headband or other headgear to keep the mask in position, something patients frequently find uncomfortable, particularly when sleeping. Such face masks are constructed to seal against the patient's face and sometimes chafe against the patient's skin which may cause facial sores, particularly if the patient's sleep pattern involves movement and repositioning during the night. Further, the seal against the patient's face may leak thus reducing or eliminating the efficacy of the device.

Some face mask designs are intended to apply pressure to the sinus areas of the face adjacent the nose, causing the airways to narrow, thereby increasing the velocity of flow through the airway, but decreasing the pressure against the nasal mucosal walls. This process tends to strip moisture from the mucosal wall during inspiration thus drying the wall and producing a burning sensation. Consequently, many patients find the face mask uncomfortable, somewhat ineffective and often results in the patient discontinuing that therapy.

Examples of nasal masks are shown in U.S. Pat. Nos. 5,335,654 and 5,535,739 to Rapoport which describes a CPAP system using a conventional nasal mask.

It has also been proposed to provide nasal pillows which are pressed against the interior portion of the nares to close the nostril openings. Nasal pillows require a robust headband or harness to maintain the pressure thus, often leading to discomfort similar to that suffered by use of the face masks.

U.S. Pat. No. 4,782,832 to Trimble discloses nasal pillows held in a patient's nose by a harness arrangement and incorporating two accordion or bellows shaped nipples for fitting against the nostril openings.

It has been recognized that nasal Expiratory Positive Airway Pressure (EPAP) may tend to maintain the patient's airways open during sleep to treat apnea conditions. Different devices have been proposed in effort to provide EPAP, including elongated adhesive strips mounting in the central area a one way valve intended to be placed over the nostrils when retiring. The device is intended to allow the valve to open as a patient inhales but as the patient exhales, close the valve to create a back pressure in hopes of opening the airways to relieve snoring. Such devices, while appearing to offer relief in theory, suffer the shortcoming that the single valve is ineffective to properly control flow through both the patient's nostrils and testing shows that the adhesive strip is challenging to apply and maintain in position during the sleep period.

CPAP is the preferred initial treatment for most people with Obstructive Sleep Apnea. With CPAP, patients wear a mask over the nose and/or mouth. An air-blower forces air into a mask and through the nose and/or mouth. The pressure is adjusted so that it is just enough to prevent the upper airway tissues from collapsing during sleep. The pressure is constant and continuous. CPAP prevents airway closure in use, but apnea episodes return when CPAP is stopped or is used improperly. Patients typically find such masks cumbersome, bulky, uncomfortable, noisy and in need of daily cleaning thus discouraging continuous use.

Other devices have been proposed such as mandibular appliances for patients with mild sleep apnea, dental appliances that prevent the tongue from blocking the throat and/or advance the lower jaw forward. These devices help keep the airway open during sleep.

In effort to avoid the discomfort of CPAP masks, it has also been proposed to provide individual nasal adhesive patches with individual one way valves to be adhered to the patient's nostrils to generate a back pressure upon exhaling. Such devices, while promising in theory, are not adequately affixed to the nostrils in such a manner such as to provide positive lodging in the nasal passage and to positively block flow upon exhaling.

Other efforts to avoid the dreaded CPAP machine proposes an exterior adhesive strip to be applied transversely across the patient's nose and configured with a spring like band to purportedly hold open and extend the nasal passages. Such devices fail to effectively address the issues of sleep apnea.

Chronic Obstructive Pulmonary Disease (COPD) includes chronic bronchitis, emphysema and asthma. In both chronic bronchitis and emphysema, air flow obstruction limits the patient's airflow during exhalation. COPD is a progressive disease characterized by a worsening base line respiratory status over the period of many years with sporadic exacerbations often requiring hospitalization. Early symptoms include increased sputum production and sporadic acute exacerbations characterized by increased cough, purulent sputum, wheezing and fever. Late in the course of the disease, the patient may develop hypercapnia, hypoxemia, cor pulmonale with right-sided heart failure and edema.

Pulmonary rehabilitation is frequently used to treat patients suffering from a variety of medical ailments such as those mentioned. For example, COPD patients are taught new breathing techniques that reduce hyperinflation of the lungs and relive expiratory airflow obstructions. Typically, these new breathing techniques include diaphragmatic and pursed-lip breathing. Pursed-lip breathing involves inhaling slowly through the nose and exhaling through pursed-lips (as if one were whistling), taking two or three times as long to exhale as to inhale. Most COPD patients instinctively learn how to perform pursed-lip breathing in order to relieve their dyspnea. It is believed that producing a proximal obstruction (e.g. pursing the lips) splits open the distal airways that have lost their tethering in certain diseased states.

It has been reported that pursed-lip breathing by COPD patients results in a reduction in respiratory rate and an increase in tidal volumes and an improvement of oxygen saturation. However, pursed-lip breathing requires conscious effort, thus the patient cannot breathe through the pursed lips while sleeping. As a result, the patient can still become hypoxic at night and may develop pulmonary hypertension and other sequelae as a result.

Non-invasive Positive Pressure Ventilation (NPPV) is another method of treating diseases that benefit from regulation of the patient's respiration. NPPV refers to ventilation delivered by a mask, nasal prongs, pillows or face mask. NPPV eliminates the need for intubation or tracheostomy.

NPPV can deliver a set pressure during each respiratory cycle, with the possibility of additional inspiratory pressure support in the case of bi-level devices. It is recognized that most patients experience difficulty adapting to nocturnal NPPV leading to poor compliance. Mask discomfort is a very common problem for patients new to NPPV, because the high pressure om the nose, mouth and face and because the tight straps are uncomfortable.

Both the pursed-lip breathing and the use of NPPV have been shown to offer significant clinical benefits to patients with a variety of medical illnesses including COPD, heart failure, pulmonary edema, sleep apnea and other sleep breathing disorders. Expiratory resistance is believed to provide the bulk of clinical improvements when using pursed-lip breathing and NPPV, through a variety of physiological mechanisms. For example, in COPD expiratory resistance is believed to facilitate expiration, increase tidal volume and decreases respiratory rate. Various devices have been proposed for applying positive pressure to the patient's nostrils and even for balancing flow between the two nostrils. See U.S. Pat. No. 5,740,799 to Nielsen.

It has been proposed to extend the expiratory time in effort to reduce the respiratory rate as by incorporating a flap valve in a nasal device for restricting exhalation flow and facilitating connection to an oxygen source. A device of this type is shown in U.S. Pat. No. 7,856,979 to Doshi. While proposing a degree of restriction during exhalation, Doshi fails to show a device and method of use to fully block exhalation so that a patient might benefit from his or her own biological responses to self-regulate during the inspiration/expiration cycle.

Furthermore, Doshi teaches a relatively undefined construction for his so-called airflow resistor and adopts the rather traditional approach of incorporating a face mask or straps or hold-fasts or the like necessary to hold the resistor in position. There have been many efforts in the art to provide a nasal device which closely fits the nasal passages for a seal around the nares and which are comfortable for the wearer. With the prior art, the experience has been that even with securement straps, the nasal devices often dislodge from the nares. It is recognized that it is beneficial and therapeutic to supply a sufficient air flow rate of respiratory air to maintain a minimum level of air volume in the lungs. If the air volume in the lungs falls below the minimum level the lungs may collapse which may be extremely dangerous or even deadly to a patient. Moreover, the back pressure can increase oxygen levels in the lungs and decrease carbon dioxide levels. This will also improve Ph by removal of carbon dioxide which is an acid, from the blood.

Many different configurations of CPAP devices have been proposed, including face mask, nasal prongs and nasal cannulas, each having advantages and disadvantages, it has been an objective of the art to devise a comfortable nasal cannula which is economical to manufacture and practical to use. Prior art nasal cannulas have been disclosed in many forms with various methods of securing the device to the nasal passageway. One such cannula assembly is disclosed in U.S. Pat. No. 3,513,844 which uses an adjustable strap that encircles the individuals head. A similar device is disclosed in U.S. Pat. No. 4,106,505 wherein the supply tubes to the cannula are hooked over an individual's ears and around the head, Even more cumbersome is the device disclosed in U.S. Pat. No. 5,477,852 incorporating a head-band for holding and positioning the nasal inserts and associated supply tubes. Yet another system in U.S. Pat. No. 5,271,391 discloses a cannula which is secured by applying strips of pressure sensitive adhesive tape to the supply tubes leading from each side of the cannula, thereby attaching the supply tubes to the cheeks of an individual with a cannula positioned in between. These head harness devices are commonly used to hold the CPAP prongs in place.

Other efforts have led to the proposal of CPAP devices for treatment of sleep apnea with relatively stiff or rigid nasal cannula surrounded by inflatable cuffs to retain the cannula in the pares as shown in U.S. Pat. Nos. 5,269,296; 5,477,852 and 5,687,715 to Landis.

However, these prior methods, are in some cases, rather complicated and expensive to manufacture and in the other cases, ineffective to secure the cannula in place without cumbersome head gear. Some apply pressure to an individual's nose and upper lip thereby causing pressure necrosis in the upper center of the nose. Many of the head harnesses fail to adequately keep the prongs in position, particularly with infants or patients who tend to roll around or move during the sleep phase. The discomfort of head harnesses and the like can often lead to the patient intentionally or unintentionally removing the harness and disconnecting the device thereby leading to sleep apnea, distractions, bradycardia, or hypoxia which is known as a dangerously low oxygen level in the blood. In practice, the tubing for many of these head harness devices is typically draped around both sides of the patient's cheek which means that the most comfortable lying position is on the patient's back thus producing a tendency to snore and create a uncomfortable sleeping position for the patient.

Other efforts to develop satisfactory anchoring systems include adhesive devices which attach directly to the nose. U.S. Pat. No. 4,823,789 discloses a nose tube anchoring strip which has an adhesive coated strip to fit over the individual's nose and an appendage for holding a nasal-gastric tube in place. A similar device is found in U.S. Pat. No. 5,156,641 disclosing an anchoring cord adhesively attached to an individual's nose at one end and attached to hold the naso-gastric catheter at the other end. U.S. Pat. No. 5,138,635 provides an anchoring device with a body engagement portion which adheres across the nose of an individual with cannula engaging portions extending downwardly.

One of the challenges met by artisans in seeking to develop a satisfactory apnea device is, to provide a device which affords adequate air flow while avoiding the necessity of applying uncomfortable head harnesses, masks and the like to hold the device in place within the nasal passages. A particular problem is the discomfort associated with the use of such devices. That is, the artisan is faced with the dilemma that a nasal device must be of sufficient structural integrity to maintain a central flow passage sufficient as to afford a high rate of flow during an expiration while, at the same time, providing comfort within the nasal passage as will be recognized abrupt changes in cross sectional shape of the cannula device, as such as presented by the end of a rigid wall, over time, create irritation within the soft tissues of the nasal passage thereby discouraging continuous use and even resulting in an unconscious desire by the patient to involuntarily remove the device during the sleep period. Until now the artisan has been faced with the dilemma of sacrificing rigidity in the cannula to achieve comfort of seeking to devise a cannula with varying rigidity.

This issue of discomfort in the nasal passages has plagued the art for some time. Numerous different approaches have been taken in effort to solve the dilemma of anchoring the nasal devices in place in a manner which will not excessively contribute to the patient's discomfort while providing a robust flow passage.

As an example, U.S. Pat. No. 4,823,789 discloses an adhesive device to attach directly to the nose via an adhesive coated sheet including an appendage for holding the naso-gastric tube. In this regard, it has been proposed to provide sponge-like nasal tips which are manually compressible to reduce the size for convenience of insertion and having a relatively slow rate of expansion seeking to block the nasal passage. A device of this type is shown in U.S. Pat. No. 4,648,398 to Agdenowski. Devices of this type, while having a sealing capability are relatively cumbersome and fail to address the issue of high rates of flow in the flow passage.

Other efforts have led to the proposal that a nasal buff be provided with external nasal sealing means which incorporate pliable, conical nare pillows to be constructed of rigid, synthetic resin material and include a bellows arrangement for accommodating the various orientations of the nasal passage or a nasal pillow constructed of a soft resin such as cell foam or gel filled with skin materials or silicone. Such devices, while providing some comfort in accessing the orifici at the distal extremity of the nasal passages, fail to address the complications relating to high flow rate and convenient retention in the nasal passages without complicated tubing and headgear.

Other proposals have been made for a tubing system to surround the user's head or neck and carrying a crescent shaped tube device in the frontal area with upwardly projecting tubes for telescopically receiving tubular nasal elements formed at their proximal extremities with enlarged rims. A device of this type is shown in U.S. Pat. No. 6,478,026 to Wood. Such devices incorporate relatively complicated valving systems and, furthermore, are cumbersome to use and can readily generate discomfort in the nasal passages due to the misalignment between the orientation of the patient's nasal passages and the device itself.

It has also been proposed that in the unrelated art of medicine inhalers to incorporate a nasal interface tube with left and right nasal prongs that pinch the nasal septum in order to retain the device in place. A device of this type is shown in U.S. Patent Application Publication No. 2002/0046751.

In recognition of shortcomings of the interface with the patient's nostrils and sealing capabilities, it has been proposed to provide a harness mounting nasal tubes which mount at the interface with then nasal passages various fittings which abut or only slightly penetrate the nasal passage. A device of this type is shown in U.S. Pat. No. 8,136,527 to Wondka. These devices are also relatively cumbersome in that the harness typically involves a connection about the patient's ears, around his or her neck and little attention is given to the sealing characteristics of the peripheral of the nasal devices with the nasal tissues or any consideration to possible discomfort deep in the nasal passages.

Other devices have been proposed for releasing oxygen only during inhalation. A device of this type is shown in U.S. Pat. No. 8,365,736 also to Doshi.

Other devices, such as ball valves have been proposed for interrupting oxygen supply during the patient's exhale phase. A device of this type is shown in U.S. Patent Application Publication No. 2008/0142012 to Fansworth.

It has been recognized that debris can build up in a valving arrangement of a face mask and that the consequent pressure build up can be relieved through a side vent of a control valve and an anti-asphyxia bypass feature. A device of this type is shown in U.S. Pat. No. 7,559,326 to Smith. Devices of this type, while tending to serve their intended purpose, suffer the shortcoming that some patients resist use of a mask covering a portion of the patient's face and the fact that failure to totally block exhalation fails to afford effective relief from a patient suffering from sleep apnea.

In unrelated art, relatively large diameter tracheotomy valves have been proposed which include diaphragms spaced some distance from the end of the valve body for opening when a negative pressure has been applied. A device of this type is shown in U.S. Pat. No. 8,051,853 to Bare. To Applicant's knowledge, such devices have not been incorporated in sleep apnea nasal devices or sized or configured in such a way as to be so incorporated.

It is believed that at least some forms of sleep apnea may be treated by fully and completely blocking the patient's exhalation while allowing for free inhaling at a relatively high flow rate.

There thus remains a need for a device of this type which is convenient for a patient to apply but which will protectively and fully block the patient's exhalation without otherwise interfering with breathing.

SUMMARY OF THE INVENTION

The present invention includes nasal tube devices formed with respective bodies for receipt in a patient's nasal passages and configured to be held in place. The bodies are relatively rigid and configured with passages surrounded by proximally facing valve seats and flexible membranes carried from the body so the peripheral edges thereof will be carried away from the respective seats during inhaling but to seat against the seats during exhalation to fully block exhaling to thereby facilitate self-regulation of the patient's breathing to treat apnea. The relatively rigid bodies are surrounded by relatively soft, pliable sheaths which project beyond the proximal ends of the respective bodies to form respective cushions.

The method of the present invention includes selecting a relatively rigid tubular body including a distal extremity formed with a shell of a predetermined outside diameter, selecting a barrel having a proximal gland formed of an inside diameter to friction fit on the shell and a distal gland of a selected inside diameter, selecting a retainer formed with airflow apertures and a central hub and a peripheral ring configured with an outside diameter formed to friction fit in the distal gland, selecting a flexible sealing membrane configured with a peripheral area to sealingly engage the seat, pinning the central portion of the membrane to the retainer and friction fitting the elements together and mounting in a holder formed with relatively soft, pliable sheaths sized to friction fit on the body and project proximally thereof to form a cushion.

BRIEF DESCRIPTION OF THE DRAWINGS

FIG. 1 is a perspective view of a nasal tube device embodying the present invention;

FIG. 2 is a top plan view of the device shown in FIG. 1;

FIG. 3 is a bottom plan view of the device shown in FIG. 1;

FIG. 4 is a transverse sectional view, in enlarged scale, taken along the lines 4-4 of FIG. 2;

FIG. 5 is a perspective exploded view, of the device shown in FIG. 1;

FIG. 16 is a perspective view of a further embodiment of the device of the present invention;

FIG. 17 is a partial top plan view, in enlarged scale, of the device shown in FIG. 16;

DETAILED DESCRIPTION OF THE PREFERRED EMBODIMENTS

Figure 6:
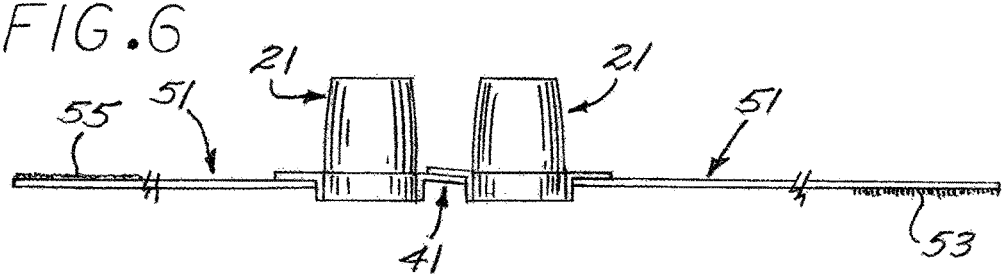
FIG. 6 is a broken side view, in reduced scale, of a pair of cannula devices shown in FIG. 1 and coupled together.

In one preferred embodiment, the present invention incorporates a pair of nasal tube devices including elongated tubular housings 21 capped at the distal end by a relatively rigid rim device 23 supported distended radially by means of radial ribs 25 and carrying a flexible membrane 27 centrally from a mounting post 29. The rim device 23 forms a proximally facing circular valve seat 31 (FIG. 4) such that when the patient inhales the diametrically opposite sections of the membrane 27 will be raised proximally off the seat 31 for the patient to inhale ambient air and, upon expiration, the membrane 27 will be driven distally to engage the peripheral edges with the seat 31 to positively block expiration of spent air. Preferably, the rim device 23 is constructed to dispose the membrane 31 in close space relationship with the end of the respective housing 21, preferably on the order of 3-6 mm from the end of such housing.

Obstructive Sleep Apnea (OSA), afflicts some 22 million Americans and a quarter of a billion people worldwide. Continuous Positive Airway Pressure (CPAP) is a recognized procedure for treating OSA and involves the application of pressure to a facemask or nasal insert such as by a pump, oxygen supply or the like to thereby apply positive pressure to the patient's nasal passage. I have discovered that certain types of sleep apnea can best be treated by harnessing the patient's own individual specific biological response to back-pressure during the exhalation of spent air. By blocking escape of air from the patient's nasal passages during the normal cycle of breathing (inspiration/expiration) the patient's own expiration pressure can be harnessed for treating sleep apnea. I refer to this procedure as the Nussbaum Nasal Auto Continuous Positive Air Pressure (NNA-CPAP). The present invention is directed to a device for carrying out thus treatment.

Figure 8:
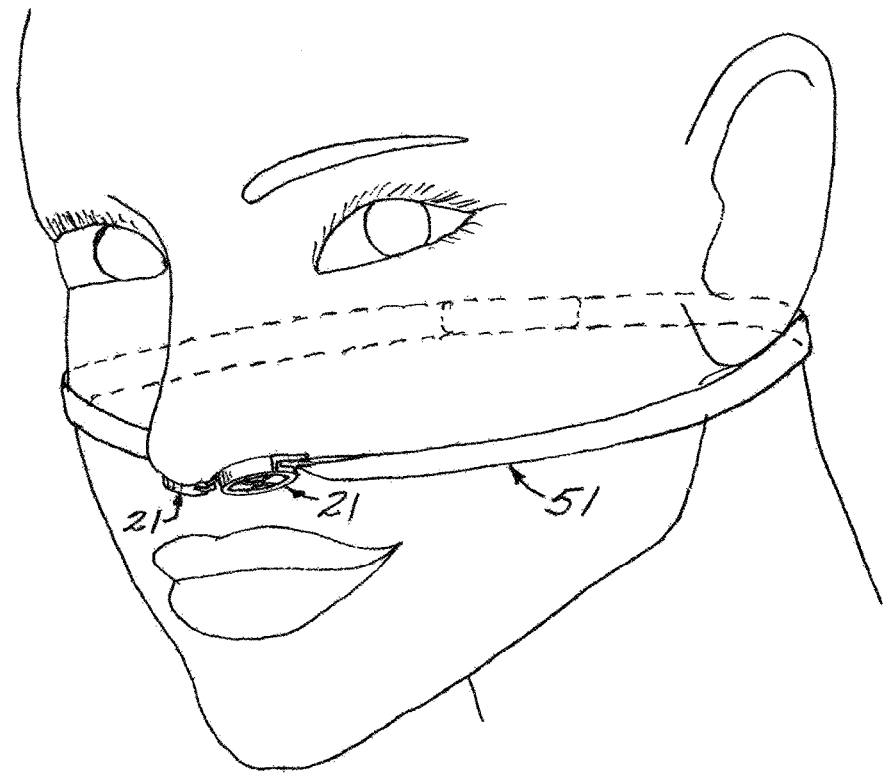
FIG. 8 is a perspective view, in reduced scale, of the device shown in FIG. 1 connected to a patient by means of a band.
Figure 9:
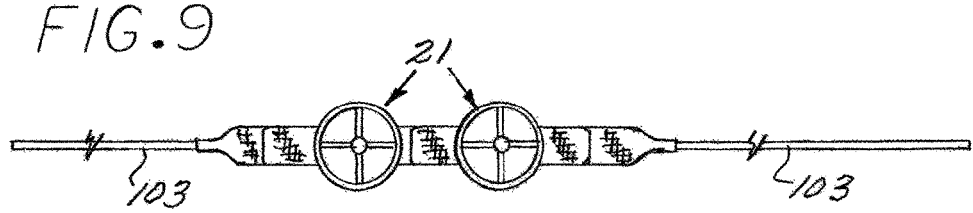
FIG. 9 is a broken bottom view similar to FIG. 7 but showing a second embodiment.

Referring to FIGS. 1, 6 and 8, in one of my preferred embodiments, I provide a pair of elongated tubular housings 21 to be inserted in the patient's nasal passages as shown in FIG. 8 to be frictionally held therein. The housings are connected together by means of an adjustable nose strap device, generally designated 41. The strap may be constructed of hook and pile connectors or possibly a belt device formed with bores spaced therealong for receipt of nubbins formed with a connector strap.

Referring to FIGS. 1, 3 and 6, the opposite sides of the respective housings 21 carry respective connector tabs, generally designated 45, incorporating hook and pile fasteners for connection to hook and pile fasteners formed on the proximate ends of respective connector straps, generally designated 51. The connector straps 51 are formed at their free extremities with hook and pile connectors 53 and 55 configured to connect together at the back of the patient's head as shown in FIG. 8.

The housings 21 are tubular shaped and formed with robust, through internal passages 61 (FIG. 5) and having their walls constructed at the proximal extremity 53 of pliable material such as a soft polymeric or elastomeric material, as for example, polypropylene or polyethylene to resistively conform to the shape of the specific patient's nasal passage to be held in place within the respective nostrils.

The walls at the distal extremity of the housings 21 may be formed of more rigid polymeric material to thus inherently maintain its circular shape so that the seat 31 could be formed in the body itself and held in a circular configuration against the pressure of the walls of the nasal passage for positive sealing with the cannular membrane. In one embodiment I form the housing with interior diametrical struts 65 for cooperating in holding the wall distended outwardly against the walls of the particular nostril to maintain a firm frictional engagement to hold the housing in place and prevent leakage between the interface of the nostril and exterior surface of the housing. It will be appreciated that the overall shape of the membrane should complement the shape of the seat.

Referring to FIG. 4, in this exemplary embodiment, the proximal extremity of the body is undercut in its exterior to form a reduced-in-diameter short shell 67 terminating in a top annular edge 75. The proximal end of the undercut forms a radially outwardly opening gland 80 terminating in its proximal end in a distally facing annular shoulder 68.

The rim device 23 includes an annular barrel device 71 formed by a concentric ring 74 configured internally with an annular stub flange 76 to sit on the top edge 75. The rim device 23 is formed medially with a radially, inwardly projecting flange 76 sitting on the edge 75, terminating in an annular edge 78 of the same diameter as the interior surface of the housing and disposed flush therewith and further formed with a distally facing annular surface 73. The barrel 71 is configured to on its proximal end with an interior diameter to form an interference friction fit with the exterior diameter of the shell 67 and projects upwardly therefrom to form an annular, inwardly opening gland 81 to receive the shell 67.

The membrane 27 is formed from a memory material and with an outside diameter to nest freely in the inner diameter of the housing to clear the inside diameter defined by the annular edge 78 of the flange 76 for free movement of the periphery relative to the seat.

With continued reference to FIG. 4, the rim device includes a retainer device 26 constructed of a hard polymeric and configured with an annular rim 86 with cruciform spokes 25 radiating outwardly from a central hub 85 having a bore therein for slip fit receipt of the female portion 87 of the fastener 29.

Referring to FIG. 5, the membrane 27 is configured centrally with a through bore 91 formed for receipt of a stem 93 of a male portion 95 of the fastener 29.

The retainer device 26 is further configured so the annular rim 86, FIG. 4, circumscribes the radially outer ends of the spokes and nests in the gland 81. The rim 86 is formed with a sufficient radial thickness to overhang radially inwardly of the annular edge 78 of the flange 76 to cause the proximally facing annular surface thereof to form the proximally facing seat 31 against which the outer periphery of the membrane 27 will abut when drawn distally to the solid line position shown in FIG. 4 to seal evenly entirely about the periphery.

Referring to FIG. 5, the membrane 27 is configured centrally with a through bore 91 formed for receipt of a stem 93 of a male portion 95 of the fastener 29.

Figure 7:
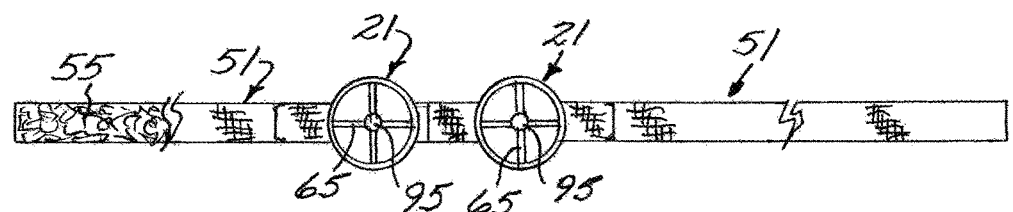
FIG. 7 is a broken bottom view of the device shown in FIG. 6.

Referring to FIGS. 6, 7 and 8, it will be appreciated that the fastener straps 51 are sized to cooperate with the tubular housings 21 and connector tab device 41 to fit around the wearer's head as shown in FIG. 8 for the hook and pile fastener strips 53 and 55 to be fastened together at the back of the head to conveniently hold the nasal cannulae in place.

In operation, the patient suffering from obstructive apnea can easily don the sleep apnea device of the present invention by positioning the tubular housings 21 sufficiently far in the nasal passages (FIG. 8) to be held in place so that the adjustable fastener tabs 45 may be adjusted to accommodate the spaced apart positioning of such housings so that such housings will nest comfortably in the patient's nasal passages.

As the housings 21 are pressed into the nasal passages, the proximal portions 54 of the housing, being constructed of somewhat pliable material, will be compressed into a shape in accordance with the shape of the patient's nostrils to provide for comfortable setting thereof and prevent leakage around the peripheries.

Once the device has been fastened in position on the patient's head as shown in FIG. 8, the patient may breathe through his or her nose. Referring to FIGS. 1 and 8, when the patient inhales, the periphery on at least two diametrical sides of the membrane 27 will be drawn proximally away from the seat 31 against the memory position of such membrane to the broken line position shown in FIG. 4 to thereby allow free passage of air past the membrane.

The peripheral edges of the membrane will thus seat evenly around the periphery against the seat 31 to block flow of spent air from the patient. This then serves to, on each exhalation cycle, provide positive air pressure in accordance with the particular biological characteristics of the patient, i.e. size, weight, lung capacity and strength, lung volume and breathing cycle. The results are comparable to those of CPAP but without the necessity of applying external pressure, pump devices and face masks or paraphernalia.

With continued reference to FIG. 4, it will be appreciated that in this preferred embodiment, when the patient inhales, the membrane will bend proximally to cause the pressure differential across the membrane to flex the peripheral edges away from the seat 31 in umbrella fashion to allow for airflow past the seat and past the exterior peripheral edges of the membrane and through the respective tubular devices. Then, upon exhalation, the pressure differential across the membrane, in combination with the memory of the membrane itself, will cause the peripheral edges of the membrane to be driven distally to engage the seat 31 entirely around the periphery to thereby positively and fully stop exhalation and allow the pressure to build up in the patient's air passages and lungs.

Figure 10:
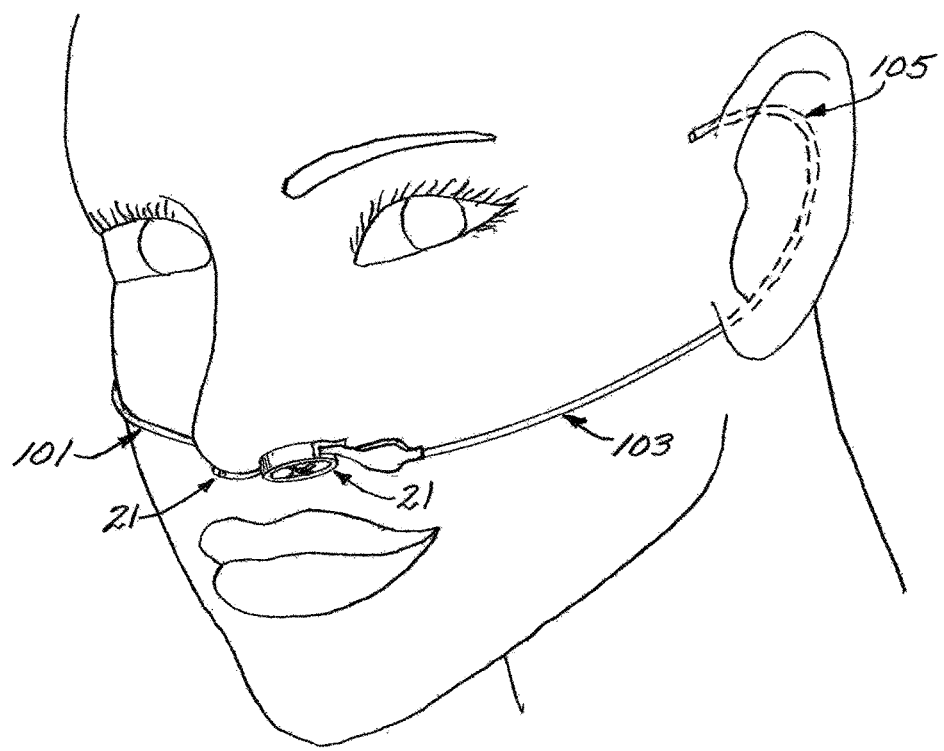
FIG. 10 is a perspective view, in reduced scale, of the device of FIG. 9 mounted to a user's head.

In some embodiments I incorporate different configurations for my fasteners to hold the device in place on the patient's head. For instance, as shown in FIG. 10, I incorporate flexible resilient ear pieces 101 and 103 which curve upwardly and rearwardly to form respective hooks 105 on the free extremities thereof to hook under and around the patient's ear, not unlike an inverted ear piece of conventional eyeglasses.

Figure 11:
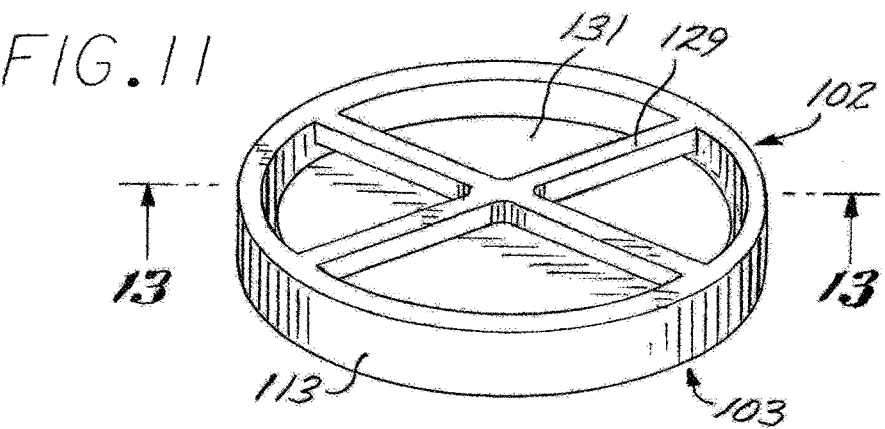
FIG. 11 is a perspective view of a valve arrangement which may employed with the nasal device shown in FIG. 1.
Figure 12:
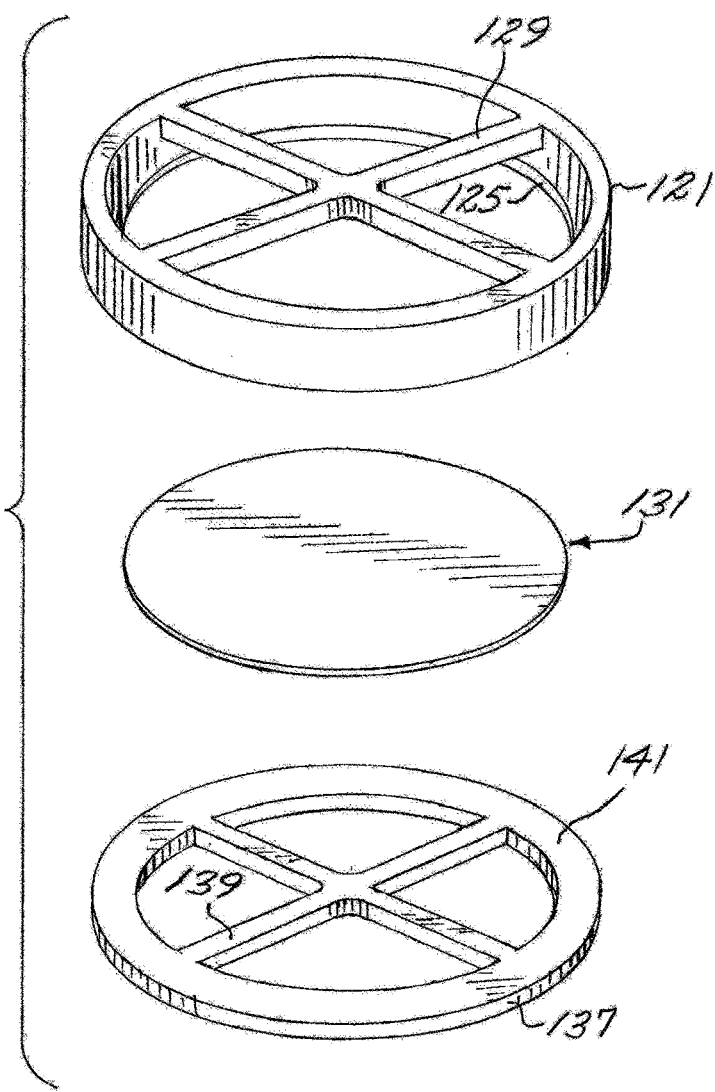
FIG. 12 is an exploded view of the valve device shown in FIG. 11.
Figure 13:
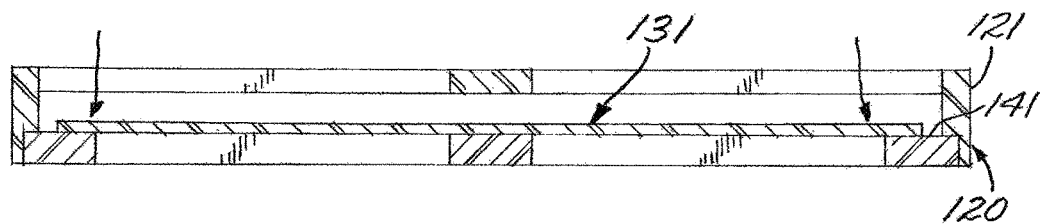
FIG. 13 is a transverse sectional view, in enlarged scale, taken along the line 13-13 of FIG. 11 and showing the valve in its closed position.

A second preferred embodiment of the head mounted sleep apnea device of the present invention is shown in FIGS. 11-13. This device incorporates a nasal tubular housing, generally designated 101, (FIG. 15) similar to the housings 21 and configured to mount valve devices 103 at the distal extremities thereof. While only a single housing is shown, as will be apparent to those of skill, a device typically includes a pair of housings similar to the housings 21. The housing 101 is formed internally with flexible, diametrical struts 105 to lend some support against total collapse but cooperating to provide for flexibility of housing walls to accommodate the shape of the patient's nasal passages and to maintain distension thereof to maintain functional engagement with the walls of the nostril.

The wall of the housing 101 is formed in the exterior of the proximal end with an annular undercut 107 defining a cylindrical shell 113 configured at its proximal end with a distally facing annular shoulder 109. The shell device terminates at its distal end in a distally facing end 114. The valve device includes a cage 102 constructed of a hard polymeric and mounted to a rim device, generally designated 104, configured with a short cylindrical barrel 116 received within the gland defined by the undercut 107 to abut the shoulder 109. The barrel is configured interiorly with an annular rib 115 constructed to abut the distal end 114.

Figure 15:
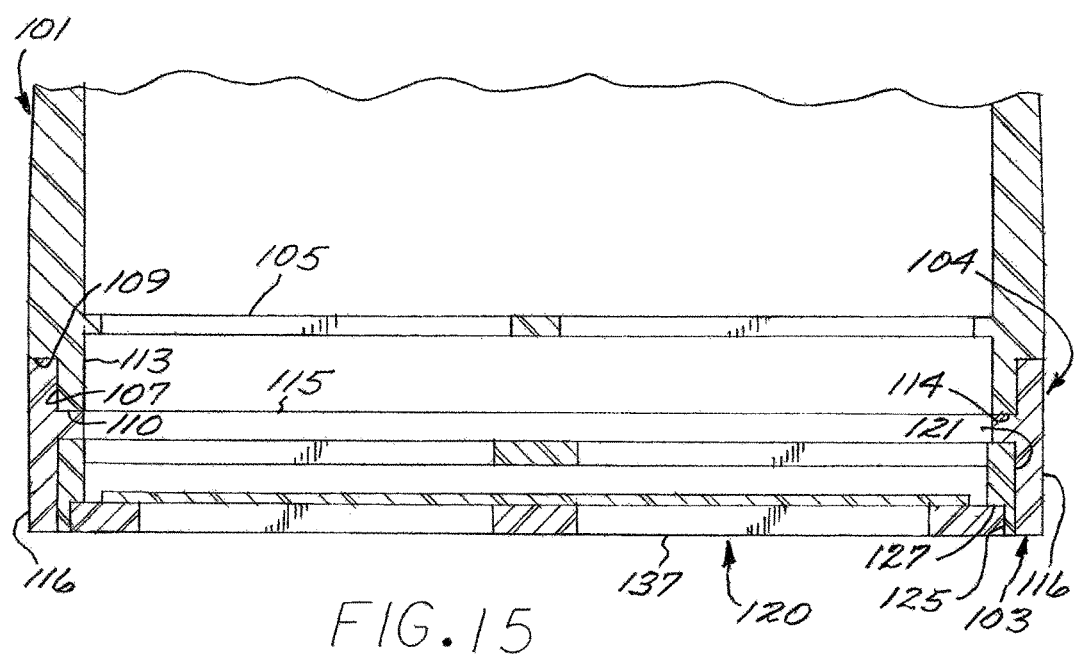
FIG. 15 is a vertical sectional view of the valve shown in FIG. 13 coupled to a nasal tube device similar to that shown in FIG. 1.

The cage is formed with close spaced proximal and distal walls, the proximal wall including an annular ring 121, received concentrically in the shell barrel 116 and the distal wall formed by a retainer ring device, generally designated 135, cooperating to cage a membrane 131 to float proximally and distally with the patient's normal breathing. The ring 121 is configured with a proximally facing, internal, annular gland 125 configured with a proximally facing annular shoulder 127 (FIG. 15).

Formed integrally with the ring 121 is a network of relatively rigid radial spokes 129. In this preferred embodiment, I show four cruciform shaped spokes 129. In practice, the number of spokes are selected in accordance with the deign parameters of the artisan and typically incorporate a network of eight radially projecting spokes to provide support for the flexible membrane.

A retainer ring device 137 is received in the gland 125 to abut the shoulder 127 and is formed on its proximal side with a proximally facing annular seat 141 configured to mate with and support the peripheral circular edge of the membrane 131 when the patient exhales as shown in FIG. 13. The ring device 137 is formed with a plurality of spokes 139 to contain the membrane.

In this embodiment the space between the facing surfaces of the walls defined by the spokes 129 and 139 is 0.3 mm but may have a greater thickness, as for instance about 0.5 to about 1.0 mm. to allow room for working of the membrane without folding or wrinkling thereof. It is understood that this cage space may vary, it only be important that the membrane 131 be contained for a rapid response to the patient's breathing and to restrict movement which might cause the peripheral edges to move out of alignment with the seat 141.

In one embodiment the membrane 131 is constructed of flexible polymeric material having a memory and sufficient body to be self-supporting but sufficiently light to be floated about in response to the patient's breathing. It is constructed with a diameter smaller than the interior of the diameter of the rim 121 for flow of atmospheric air between such interior diameter and the outside diameter of such membrane shown in FIG. 14.

Figure 14:
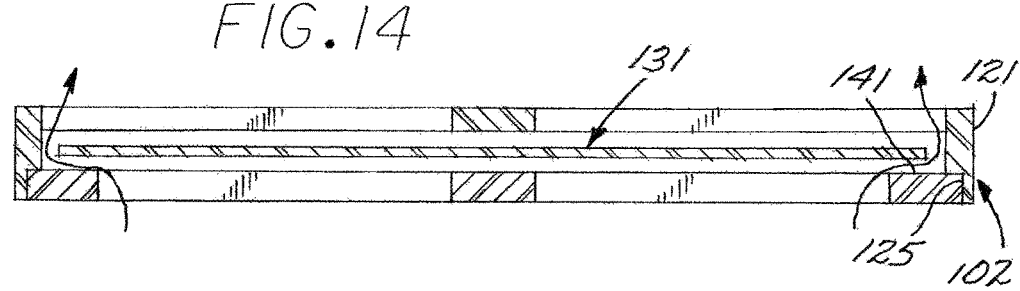
FIG. 14 is a vertical sectional view similar to FIG. 13 but depicted the valve in its open position.

As noted, the membrane 131 is relatively thin and constructed with a minimal mass such that when the patent inhales, as shown in FIG. 14, the pressure differential across the membrane will readily lift the membrane off the seat 141 with minimal resistance thus presenting little or no interference with the inhalation by the patient but yet serving to positively seal about its periphery to the seat 141. In some embodiments the membrane is constructed with a rigid body to float about the cage without flexing.

In operation, a patient suffering from sleep apnea may be treated with the sleep apnea device of FIGS. 11-15. The patient may merely place the tubular housings 101 in his or her nasal passages, it being appreciated that the housing wall, struts 105, rim device 104 and spokes 129 and 139 will flex sufficiently to allow the housing to flex slightly to accommodate the transverse cross sectional shape of the patient's nasal passages. In practice, for some embodiments, I construct the membrane and seat such that any flexing of such seat out-of-round will be accommodated by the clearance between the outside diameter of the membrane and the inside diameter of the ring 121 without interfering with movement of the membrane under influence of the patient's inhaling and exhaling. In other embodiments, I construct the spokes 129 and 139 and the housing wall and rings to resist radial flexing to thus positively maintain the circular configuration for the seat 141 as the device is inserted in the patient's nasal passage.

In practice, I construct the membrane 131 with an external diameter sized to cause the peripheral edges to clear between the interior diameter of the ring 121, as well as to overlap the seat 141 such that flexing of the wall of the housing 101 and the rings 113 and 121 to an out-of-round position, say providing an eccentric configuration of 2-3 mm from the round, so the interior diameter of the ring 121 will not interfere with free travel of the membrane under influence of the patient inhaling and exhaling. Thus, with the light feather-like weight of the membrane 131 and such freedom of movement, the membrane will float freely proximally and distally with respect to the seat 141 so as to provide minimal interference with the patient's normal inhaling so as to avoid any discomfort during the inhaling cycle.

Once the housings 101 are inserted proximally in the patient's nasal passages, and a band, similar to that shown in FIG. 8, extended around the patient's head to hold the housings in place, the patient is at liberty to sleep in the normal fashion, maybe with his or her bed-partner without concern over him or herself being awakened by sleep apnea or snoring which might interfere with the bed-partner's sleep.

That is, when the patient inhales, the pressure differential across the membrane 131 as shown in FIG. 13 will lift the membrane off the seat 141 to allow the patient to draw atmospheric air into the lungs without interference.

During the exhaling cycle, however, the pressure differential across the membrane 131 will drive such membrane distally to engage the peripheral edges thereof evenly entirely around the periphery of the seat 141 to fully block exhaling by the patient. It has been found that this feature of the present invention effectively serves to treat the patient's sleep apnea without excessive interference with the patent's sleep pattern but yet in most cases provides for an uninterrupted sleep period.

With my nasal CPAP Functional Residual Capacity (FRC) will be optimized during the expiratory, as well as the inspiratory cycles. This will improve the Ventilation/Perfusion (dv/dt/dq/dt) relationships and therefore maintain adequate oxygenation where Ventilation=Air Flow=Volume of air time unit=dv/dt and Perfusion=Blood Flow=Volume of capillary blood per unit of time-dq/dt. $CO_2$ elimination is not impaired by the level of CPAP generated by this device, as CPAP values at the target range do not impair levels of expired Carbon Dioxide, called end-Tidal $CO_2$($ETCO_2$) nor does it impair the partial pressure of Carbon Dioxide in the blood ($PCO_2$).

As will be appreciated by those of skill, my device is intended to present resistance to air flow. Resistance is calculated as the driving pressure divided by air-flow. Simply stated, if pressure is P and flow is dv/dt (flow=volume of air per unit time) then Resistance is calculated as P/dv/dt or R=driving pressure/airflow presented in units of cm $H_2O$/ L/sec. Since my CPAP generates pressure in the range of 4-10 cm $H_2O$ (or between 40 and 10 mm $H_2O$) during the expiratory phase (expiration). The total pressure may be calculated by applying such pressure to a surface area with approximately 5 mm radius of nasal opening (surface area SA=3.14×5×5=78.5 $mm^2$=0.1256SI) (square inch SI=625 $mm^2$) represents maximum 10/0.1256=79.61 mm $H_2O$/ SI=0.11 PSI However, it should be noted that the nasal resistance represents 50% of total airway resistance and that airway resistance changes with lung volume, but not in a linear fashion. Increasing lung volume above FRC (Functional Residual Capacity) only minimally decreases airway resistance hence my nasal CPAP will maintain adequate pressure keeping the airway passages open during the entire respiratory cycle (inspiration and expiration). In very low lung volumes R may become higher. As will be recognized by those of skill, R also depends on acceleration (inertance) and frictional factors.

From the foregoing it will be appreciated that my discovery of a method for treating sleep apnea and a device for practicing that method provides an effective and convenient apparatus for the patient to wear without the hindrance normally associated with masks and related paraphernalia such as pressurization devices and the like.

In essence my device and procedure is directed more at the CPAP values (Pressure values) and not so much at the Resistance which can be manipulated by volume and flow variations. My nasal CPAP can be adjusted by the patient's individual lung volumes and flow, and since my device provides a positive seal, it guarantees an effective CPAP.

The embodiment shown in FIGS. 16-19 includes, generally, a relatively rigid tubular body 151 defining a through air flow passage 153 and configured at its upper extremity with a annular shell 155 mounting a barrel 157 which is surmounted by a spoked retainer 159. The retainer 159 mounts centrally therefrom a flexible circular membrane, generally designated 161. The body 151 is received in a soft, pliable, elastic sheath, generally designated 163, which projects proximally of the end 165 of the housing 153 to form an annular cushioning ring, generally designated 167.

In practice, the sheath 163 is incorporated in a holder, generally designated 171 (FIG. 16), which includes a connector strap 173 connected between a pair of sheaths 163. The bodies 151 are sized for fitting the nasal passages of a user, accommodating the respective surrounding sheaths 163. The bodies and sheaths are configured and arranged to, when inserted, slightly stretch the walls of the nasal passages to be constrained and held frictionally in place without the necessity of head straps or attachment gear so often felt uncomfortable to a user.

Then, as the patient breathes, upon inhaling, the peripheral edges of the membrane 161 will be drawn proximally to flow air around the outside of such peripheral edges to flow through the air passage 153 to the patient's lungs. Upon exhaling, the pressure differential across the membrane 161 will drive the peripheral edges thereof distally to close the membrane to airflow thereby positively blocking the flow of air during the exhalation cycle.

Figure 18:
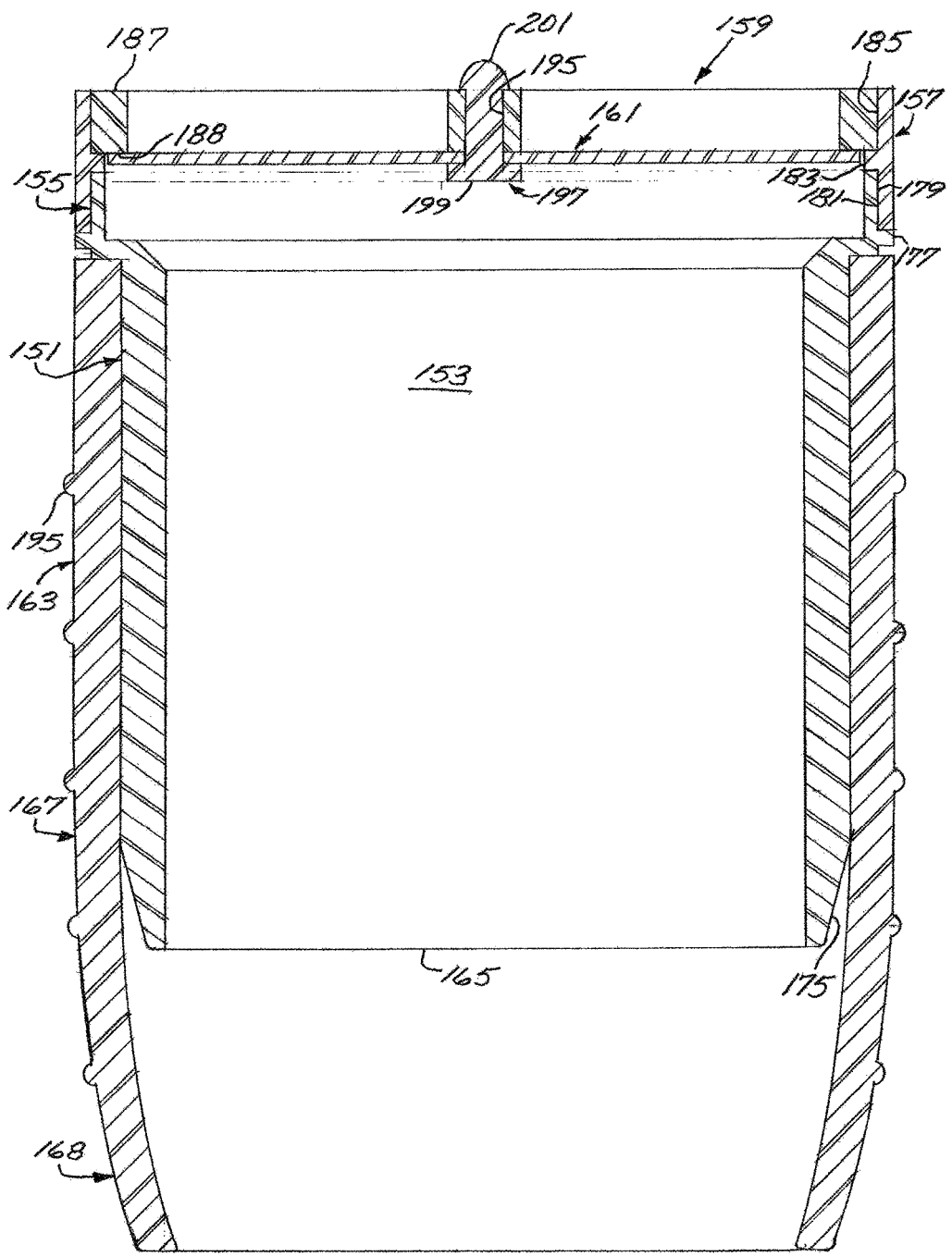
FIG. 18 is a longitudinal, sectional view, in enlarged scale, taken along the lines 18-18 of FIG. 17.
Figure 19:
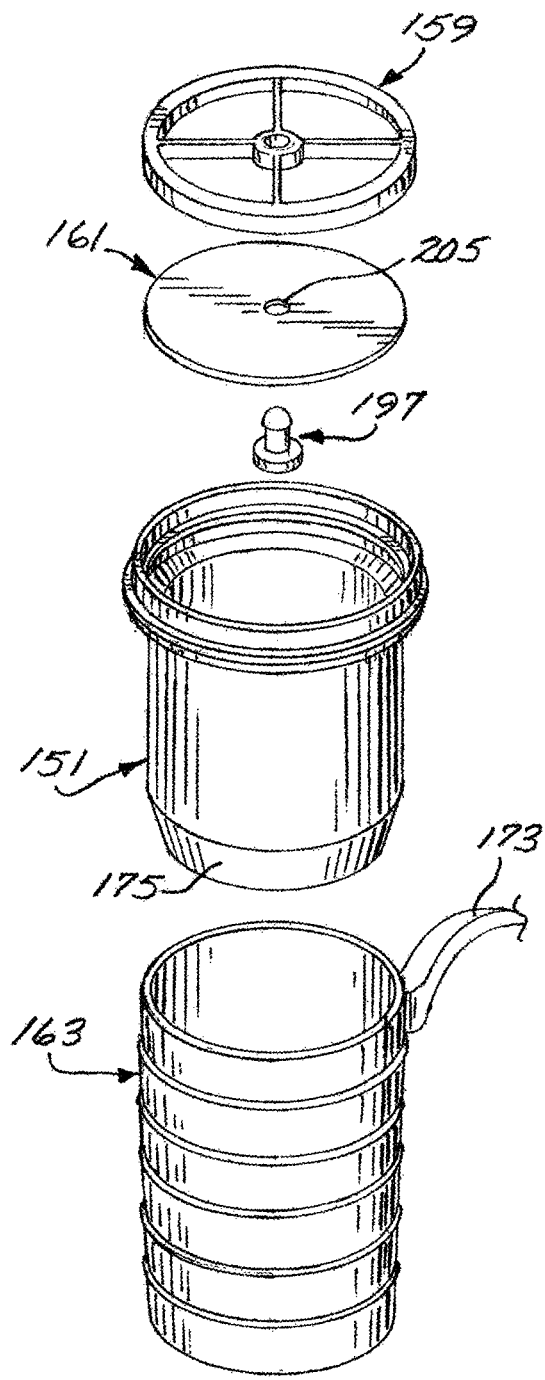
FIG. 19 is an exploded view of the device shown in FIG. 1 and depicting a method of the present invention.

Referring to the FIGS. 17,18 and 19 in detail, the body 151 is cylindrically shaped and formed proximally with an external frustoconical chamfer 175 tapering proximally, radially, inwardly and configured distally with an exterior, annular flange 177 with the shell 155 being formed therebeyond in reduced diameter to form an annular gland 179. The barrel 157 is configured proximally with a proximal gland 181 having an interior diameter slightly less than the outside diameter of the shell 179 so as to be held thereon by friction fit. The barrel 157 is formed medially with an interior annular flange 183 and distally with a distal gland 185 of a selected inside diameter.

The retainer 159 is formed with a annular peripheral ring 187 having an exterior diameter slightly larger than the interior diameter of the gland 185 to thereby be held frictionally therein. The retainer 159 is formed with internal radial spokes 191 arranged in cruciform shape and constructed with a central hub 193 configured with a thorough bore 195. The through bore 195 receives a pliable fastener 197 formed on its proximal end with an enlarged head 199 and on its distal end with a bulbous head 201 slightly larger in diameter than that of the bore 195 to thus be held in place. Referring to FIG. 19, the membrane 161 is formed with a central bore 205 which receives the fastener 197 to be anchored to the hub of the retainer 159.

The body 151 is constructed of a material having a relatively high structural integrity to maintain the walls distended during use. It has been found that medium or high density polyethylene or nylon material will perform to provide the desired rigidity. As will be appreciated by those skilled in the art, the body need not be totally rigid but may have some flexibility to accommodate the contour of the patient's nasal passage but must have sufficient rigidity to maintain distension to maintain the flow passage 153 open for unrestricted flow of air during the inhalation cycle.

As will be appreciated by those of skill, in one embodiment, the overall function of the device has various design constraints which require sufficient rigidity to maintain the air passage 153 open but yet present sufficient softness and pliability at the proximal end to provide a cushion between the end of the body and nasal surface. Moreover, to achieve the results of providing for adequate anchoring of the device, without the necessity of a head harness, it is beneficial to provide gripping elements for retaining the device in the patient's nasal passages. To that end, the sheaths 163 are constructed of low density polyethylene or equivalent material to provide for flexibility and pliability in the walls thereof such that the portion projection beyond the proximal end 165 is pliable and to flex inwardly and provide softness for cushioning against the sensitive walls of the nasal passages and avoid any abrupt discontinuity in the longitudinal profile of the device exposed to the nasal wall which, upon flexing from inhaling and exhaling during a night's sleep, would cause friction, rubbing, and discomfort to the patient which could result in the patient subconsciously pulling the device from the nasal passages to eliminate the discomfort.

For the purposes of this application, the terms are relatively rigid and relatively soft with respect to the body of the valve device and the covering sheath is intended to mean that the body itself has sufficient structural integrity to maintain its shape and possibly present some compliance with the overall shape of the patient's nostril but yet maintain its distended configuration to provide for air passage while the descriptive term relatively soft means that the sleeve is softer and more pliable than the wall of the valve device itself and it has sufficient flexibility to provide some pliability to the walls of the cushion 167 to flex with the flexing of the walls of the patient's nasal passages and prevent abrupt longitudinal profile disruption which could cause irritation to the walls of a patient's nasal passages.

The sheaths 163 are thus formed to project approximately ½ to 1 full centimeter, possibly more or less, from the distal ends 165 of the tubular bodies to thus provide the flexible cushioning effect. The walls of the sheaths 163 are furthermore constructed at the proximal extremity to curve proximally, radially inwardly to form a gently curved bullnose shaped prow 168 to facilitate insertion in the nasal passages and to also provide for a gradual transition from the end 165 of the body and minimize patient discomfort and irritation. Additionally, to further facilitate secure anchoring in the nasal passages, the exterior walls of the sheaths 163 may be formed with high friction, scarring, dimples undulations or protuberances, such as circumferential gripping ribs 195 formed in the exterior walls thereof and spaced longitudinally therealong to be pressed into the soft walls of the nasal passages to form indentations which cooperate in resisting distal dislodgement of the combination during use. It has been found that with such an arrangement, and properly sized, the device will be held firmly in position without the necessity of headgear or straps which many patients find uncomfortable, distracting and oftentimes discourage use.

To facilitate full or nearly full blockage of airflow around the outside periphery of the device of the present invention it is necessary to construct the body 151 of a selected number of different outside diameters in order to accommodate the ordinary size of nasal passages for various patients for proper functioning and control of air and also to facilitate anchoring in the nasal passage. In this regard, I have discovered that bodies 151 constructed with outside diameters of the following centimeters are desirable.

| 0.889 |
| 0.953 |
| 1.054 |
| 1.557 |
| 1.257 |
| 1.308 |

In my physical embodiment I have constructed the device with a wall thickness of 0.01 cm, it being realized by those of skill that wall thicknesses of 0.01 to 0.02 cm and even greater or smaller will suffice, to provide the desired structural integrity and compliance with the nasal passage shape.

In one preferred embodiment, I have selected an overall length for the body of 1.27 cm, it being realized that a few centimeters more or less will also suffice, depending on the particular patient category to be treated.

Also, in practice, I have constructed to membrane 161 from a sheet of polyurethane having a thickness of about 0.01 cm to provide flexibility and at least some degree of memory tending to bias the membrane to its planar position shown in FIG. 18 and having sufficient flexibility to enable the valve to open with a pressure differential thereacross of about 0.11 psi.

From the foregoing, it will be appreciated that the construction and assembly of the device of the present invention is particularly convenient and economical. That is, with the construction described, the barrel 157 may be conveniently assembled on the shell 179 by taking advantage of the interference, friction fit to quickly and efficiently secure the barrel in place as shown in FIG. 18. The membrane 161 may be conveniently attached to the hub of the retainer 159. The retainer 159 may then conveniently forced by interference fit into the gland 185 to complete the assembly ready for insertion in the respective sheaths 163. In some embodiments, I incorporate an adhesive to further affix the components together.

As described, the sheaths 163 may be constructed of flexible, pliable polyethylene having a wall thickness of about 0.02 cm and are formed to stretch under the influence of the chamber 175 of the body being inserted into therein to thereby create a friction fit with the body 151 to hold the sheaths in place.

In use, it will be appreciated that when a patient is to retire, he or she may select the device of the proper diameter to easily and conveniently apply to the nasal passages. The patient may grasp the band 173 (FIG. 16) to orient the respective sheaths 163, containing the bodies 151, with the respective nasal passages and the devices pressed proximally into the respective nasal passages thus stretching the respective nasal passages slightly to take advantage of the constrictive capacity of the walls of such passages to, when positioned, grip the exterior walls of the sheaths 163 with the ribs 195 pressed into the passage walls to thereby gently resist dislodgement of such devices distally from the passages.

The patient may then retire and his or her breathing cycle will be harnessed by the device of the present invention such that upon inhalation, the periphery of the membranes 161 will be lifted off the respective seats 188 to provide for free passage of air around the peripheral edges of the membrane with little restriction to flow freely through the passages 153 and into the patient's lungs. Then, when the patient exhales, the pressure differential across the membrane 161 will cause the periphery thereof to engage the seat 188 to thus positively block flow of air thereby taking advantage of the patient's own breathing cycle to treat his or her apnea condition. During the inhaling and exhaling cycle, the wall of the respective cushions 167 may be flexed slightly depending on the force placed on the walls of the patient's nasal passages and pressure build up within the device, which flexure will cushion against direct contact with the relatively rigid chamber 175 of the body 151 to thereby cushion against irritations to the walls of the patient's nasal passages while maintaining a positive and good seal with the walls of such passages. As will be appreciated by those skilled in the art, as a practical matter, there may be a slight bypass of air around the outside of the device during the exhaling cycle but, in practice, I have discovered that escape of 5-10% of the normal patient's air flow does not distract significantly from the overall operation of my device.

Consequently, it will be seen that the device of the present invention is relatively economical to manufacture and provides for comfortable, effective use in treating sleep apnea avoiding many of the complications which would otherwise discourage use.

Although the present invention has been described in detail with regard to the preferred embodiments and drawings thereof, it should be apparent to those of ordinary skill in the art that various adaptations and modifications of the present invention may be accomplished without departing from the spirit and the scope of the invention. Accordingly, it is to be understood that the detailed description and the accompanying drawings as set forth hereinabove are not intended to limit the breadth of the present invention.

I claim:

1. A respiratory apparatus comprising:
a pair of nasal tube devices configured with relatively rigid tubular bodies for receipt in a patient's nasal passages to cooperate in locking air flow, the bodies configured with through air-flow passages and formed with respective proximal and distal extremities, the bodies including respective rim devices formed with respective proximally facing peripheral valve seats;
respective membranes having marginal edges configured to be, when the devices are disposed in the nasal passages, responsive to the pressure differential generated by the patient inhaling to be shifted from respective open positions off the respective seats to provide for air flow through the air-flow passages and further responsive to the patient exhaling to close the marginal edges on the respective seats to fully block exhaling from the respective nasal passages;
retaining devices carried from the respective tube devices to mount the respective membranes for shifting from the respective open to the closed positions; and
relatively soft, pliable sheaths received over the respective tubular bodies and projecting proximally beyond the respective proximal extremities to form respective cushioning rings.

2. The respiratory apparatus of claim 1 wherein:
the sheaths are formed with proximally projecting radially in-turned walls defining respective prows.

3. The respiratory apparatus of claim 2 wherein:
the in-turned walls curve proximally and radially inwardly.

4. The respiratory apparatus of claim 1 wherein:
the retaining devices include radial spokes formed with apertures therebetween.

5. The respiratory apparatus of claim 1 wherein:
the membranes are constructed to, when lifted off the respective seats, accommodate airflow around the peripheries thereof.

6. The respiratory apparatus of claim 1 that includes:
pins mounting on the membranes to the respective retaining devices.

7. The respiratory apparatus of claim 1 wherein:
the membranes are flexible.

8. The respiratory apparatus of claim 1 wherein:
the membranes are constructed of memory material.

9. The respiratory device of claim 1 wherein:
the respective seats are circular; and
the membranes are circular to define circular peripheral edges and are further constructed to be responsive to the pressure differential to seal the entire extent of the peripheral edges against the respective seats.

10. The respiratory device of claim 1 wherein:
the membranes are so constructed that a differential pressure thereacross of substantially 0.11 psi will move the respective membrane relative to the valve seats.

11. The respiration apparatus of claim 1 that includes:
a gripping device to facilitate gripping to the interior walls of the respective nasal passages.

12. A method of manufacturing a respiratory apparatus including:
selecting a relatively rigid tubular body formed with a distal extremity configured with a flange defining a distally facing shoulder with a shell of a selected outside diameter projecting distally thereof;

selecting a barrel formed with a circular ring and an inside diameter of a dimension to friction fit on the shell and formed with a distal gland of a predetermined inside diameter;

selecting a circular retainer formed with a peripheral rim and cross spokes intersecting to define a central hub, the rim of an outside diameter to friction fit in the gland and formed with a proximally facing valve seat;

selecting a circular flexible valve membrane formed with an outer periphery of a dimension to contact the proximally facing seat, pinning the membrane centrally to the hub;

fitting the retainer to be frictionally held in the distal gland, fitting the barrel on the shell, fitting a stretchable, relatively soft sheath over the body and projecting it proximally of the body to firm a cushion ring whereby the body may be fitted in a patient's nostril passage with the cushion ring interposed between the body and surface of the nasal passage so that upon inhalation a pressure differential will be created across the membrane to lift it off the seat and upon exhalation, the outer periphery of the diaphragm will be driven against the seat to positively block airflow through the passage.

13. The method of claim 12 that includes:
forming the sheath with a bullnose shaped prow.

14. In combination, a sleep apnea apparatus including:
a pair of respiration devices including relatively rigid tubular bodies of respective predetermined outside transverse cross-sections and formed with respective through-passages, the bodies formed internally with an annular, proximally facing seat and terminating in respective proximal ends;

retainer devices mounted distally on the bodies and carrying centrally therefrom, respective flexible membranes configured to, when pressurized on the proximal sides, cooperate to seal against respective seats;

a holder including a pair of elastic sheaths, stretched against the predetermined transverse cross-sections to hold the respiration devices in position; and the respective sheaths projecting proximally from the respective proximal ends to form respective relatively soft cushion rings distal of the respective body ends.

15. The apparatus of claim 14 wherein:
the respective sheaths are formed to, beyond the respective proximal ends, taper distally inwardly to form respective bullnose-shaped prows.

16. Respiratory apparatus comprising:
a holder constructed of relatively soft material and including a pair of elongated tubular sheaths formed at their proximal ends with cushioning rings, the tubular sheaths connected together by a flexible strap;

relatively rigid nasal tubes constructed to be frictionally fit distally in the respective sheaths to be held frictionally in position, the tubes formed with tubular bodies configured with through airflow passages and formed with respective proximal and distal ends and formed adjacent the respective distal ends with respective distally opening annular shells of selected exterior diameters;

barrels constructed to be friction fit on the respective shells to be frictionally held thereon, the respective barrels formed with respective distally opening annular glands;

retainer devices friction fit in the respective distally opening glands, formed with through openings and proximally facing valve seats; and flexible membranes anchored to the respective retainers and configured to, when pressure differentials are applied thereto during a patient's expiration, seal against the respective valve seats.

17. A method of treating apnea including:
selecting a respiration device including a relatively rigid tubular body of a predetermined outside diameter formed with a through passage, proximally facing annular seat, and terminating in a proximal end;

selecting a retainer mounted distally on the body and carrying centrally therefrom a flexible membrane configured to, when pressurized on the proximal side cooperating to seal against the seat;

selecting an elastic sheath of an inside diameter smaller than the predetermined diameter and inserting the device in the sheath to stretch the sheath over the device to leave the sheath projecting proximally of the body to form a cushion; and inserting the body and sheath in the patient's nasal passage.

18. A method of treating sleep apnea including:
selecting a pair of respiration devices including relatively rigid bodies of respective predetermined outside transverse cross-sections formed with through-passages and formed internally with respective proximally facing annular seats and terminating in respective proximal body ends;

selecting a pair of valve members responsive to a pressure differential thereacross when the patient exhales to seal against the respective seats;

installing the valve members in the through-passages;

selecting a holder including a pair of sheaths of respective inside cross-sections smaller than the predetermined transverse cross-sections and inserting the respective devices in the sheaths to stretch the sheaths over the devices for gripping thereof;

adjusting the position of the bodies in the respective sheaths to leave the respective sheaths projecting proximally of the respective body ends to form cushions; and inserting the bodies and sheaths in the patient's nasal passages.

* * * * *